United States Patent [19]

Covington et al.

[11] 4,187,077

[45] Feb. 5, 1980

[54] CONTAINER WITH ARTICLE POSITIONING ELEMENT FOR DISPENSING REAGENT COATED SLIDES TO AN AUTOMATED ANALYZER

[75] Inventors: Roger G. Covington; Stephen H. Miller, both of Rochester; Archie J. Tucker, Middlesex, all of N.Y.

[73] Assignee: Eastman Kodak Company, Rochester, N.Y.

[21] Appl. No.: 912,665

[22] Filed: Jun. 5, 1978

[51] Int. Cl.$^2$ .............................................. G01N 1/28
[52] U.S. Cl. ...................................... 422/63; 422/57; 422/104; 221/198; 221/279
[58] Field of Search ............. 23/259, 253 R; 221/279, 221/220, 226, 229, 230, 231, 198, 238; 422/57, 63, 102, 104

[56] References Cited

U.S. PATENT DOCUMENTS

| 1,801,165 | 4/1931 | Macke | 221/238 |
| 3,115,991 | 12/1963 | Carew et al. | 221/198 |
| 3,533,744 | 10/1970 | Unger | 23/253 R |
| 3,767,083 | 10/1973 | Webb | 221/279 |
| 3,905,772 | 9/1975 | Hartnett et al. | 23/259 |

Primary Examiner—R. E. Serwin
Attorney, Agent, or Firm—M. S. Sales

[57] ABSTRACT

A container is disclosed for receiving a stack of articles to be sequentially removed from a dispensing station of the container. A stack positioning element in the container has an anti-backup member including a pair of pawls resiliently urged into engagement with cooperating ratchet teeth on opposed inner wall surfaces of the container to inhibit movement of received articles away from the container's dispensing station. A plunger may enter the container through an opening in a wall opposed to the dispensing station to provide the required force to sequentially move the stack positioning element and article stack toward the dispensing station as articles are removed therefrom.

5 Claims, 5 Drawing Figures

CONTAINER WITH ARTICLE POSITIONING ELEMENT FOR DISPENSING REAGENT COATED SLIDES TO AN AUTOMATED ANALYZER

BACKGROUND OF THE INVENTION

CROSS REFERENCE TO RELATED APPLICATIONS

Reference is made to commonly assigned, copending U.S. Patent Applications Ser. No. 751,912 entitled CHEMICAL ANALYZER, filed in the names of Louis C. Nosco, Anthony P. DiFulvio and Henry S. Adamski on Dec. 17, 1976, now abandoned; and Ser. No. 912,290 entitled ARTICLE DISPENSER APPARATUS, filed concurrently herewith in the names of G. W. Scherer and R. G. Covington.

FIELD OF THE INVENTION

The present invention relates to article containers from which individual articles can be sequentially removed from stacks of articles received in the containers.

DESCRIPTION OF THE PRIOR ART

In recent years, a number of automated systems have been developed for carrying out quantitative chemical analysis of fluid samples. While many of the commercially available systems utilize liquid reagents and require analyzer equipment having intricate solution handling and transport capabilities, one biological fluid analyzing apparatus in which discrete test slides containing individual dry reagents are metered through the apparatus to receive a drop of biological fluid to be tested is described in commonly assigned, co-pending U.S. Patent Application Ser. No. 751,912, entitled CHEMICAL ANALYZER filed on Dec. 17, 1976.

As described in that application, the test slides are stacked in containers also called cartridges. Each slide in a particular container has the same, appropriate reagent for a particular test, such as for example a reagent for testing glucose in blood serum. Other containers might house slides for other tests. One or more containers may be received in an appropriate nest of the analyzing apparatus with a spring biased plunger arranged to engage the stack of slides through an opening in the container to urge the slides forwardly toward a dispensing station at one end of the container.

A push blade in the analyzing apparatus enters the container at the dispensing station to remove the leading slide from the container by pushing it through a slot in the container wall. The remaining slides are moved forwardly in the container by the plunger as each preceding slide is removed.

It is foreseeable that, during the operation of such analyzing apparatus, situations might occur in which it would be desirable to take a container from the apparatus nest after some, but not all, of the slides have been removed therefrom. Such situations might include instances wherein a different biological test requiring a different reagent is to be conducted or wherein the slides are to be stored in controlled conditions at the end of a work day. Upon such removal of a container from the nest, the apparatus plunger no longer urges the remaining slides toward the container's dispensing station. Accordingly, the slides would be free to move about within the container; possibly becoming disoriented and causing jams when the container is again loaded into the analyzing apparatus nest.

SUMMARY OF THE INVENTION

In accordance with the present invention, we have provided a container for receiving a stack of reagent articles for sequential movement toward, and removal from, a dispensing station of the container for delivery to apparatus for carrying out quantitative chemical analysis of fluid samples. A stack positioning element located behind the article stack is movable forwardly toward the dispensing station by a plunger which enters the container through an opening in the container wall. The stack positioning element is positioned in the container between the slides and a received plunger so that the plunger pushes against the positioning element to move the element toward the dispensing station as the slides are removed from the container.

In a preferred embodiment of the present invention, a plurality of ratchet teeth on the container wall structure cooperate with resiliently urged ratchet pawl means on the positioning element to keep the element in position should the plunger be removed from the container, thereby preventing movement of the slides away from the dispensing station.

The invention, and its objects and advantages, will become more apparent in the detailed description of the preferred embodiment presented below.

BRIEF DESCRIPTION OF THE DRAWINGS

In the detailed description of the preferred embodiment of the invention presented below, reference is made to the accompanying drawings in which.

DESCRIPTION OF THE PREFERRED EMBODIMENT

Figure 1:
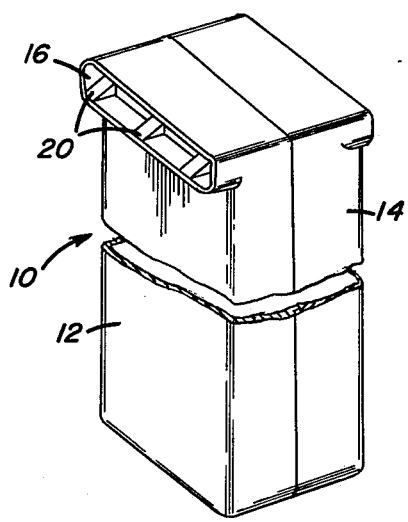
FIG. 1 is a perspective view of a slide container apparatus in accordance with a preferred embodiment of the present invention.
Figure 2:
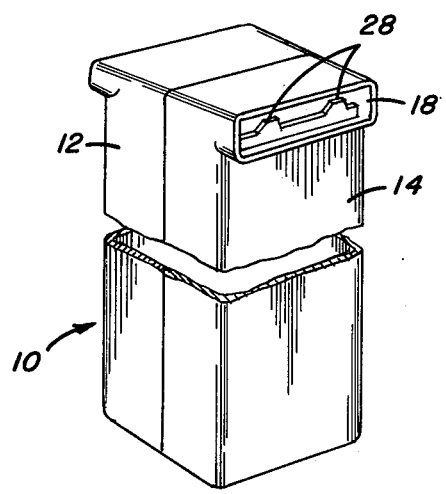
FIG. 2 is a perspective view of the apparatus of FIG. 1 taken from another angle.

In accordance with an illustrative embodiment of the present invention there is shown in FIGS. 1 and 2 a container, designated by the reference numeral 10, adapted to hold a stack of test slides for supply to a chemical analyzer such as the analyzer disclosed in aforementioned U.S. patent application Ser. No. 751,912. Container 10 includes a generally rectangular casing having two parts 12 and 14 shown separated in FIG. 3.

Figure 3:
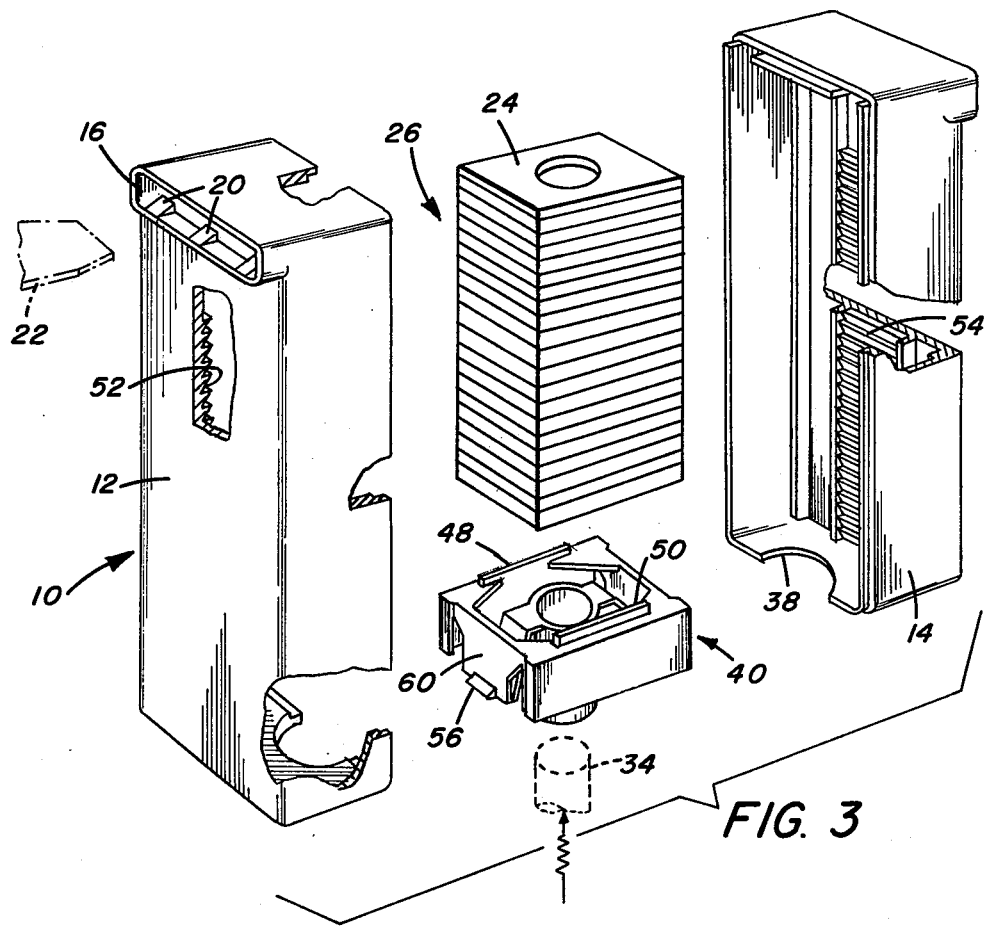
FIG. 3 is an exploded view of the apparatus of FIG. 1 showing a slide stack and a stack positioning element.

A dispensing station is provided at the forward end of container 10 (the top of the container as shown in FIGS. 1–3) and includes a pair of slots 16 and 18 for removing slides from the container. Slot 16 is ramped (three ramps 20 shown) to guide a push blade 22 of the analyzer into contact with the trailing edge of the foremost slide 24 of a slide stack 26. Slot 18 has a pair of tabs 28 which normally retain the slides in the container until pushed out by push blade 22. The push blade extends through slot 16 to push the foremost slide out of slot 18 and into automatic slide handling means, not shown, of the analyzing apparatus.

Figure 4:
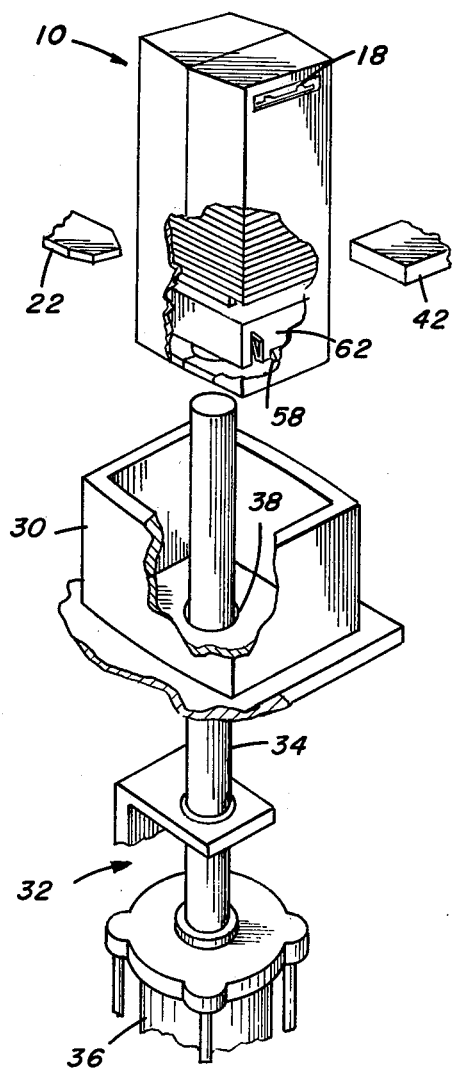
FIG. 4 is a perspective schematic view illustrating a container according to the present invention ready to be inserted into a nest for the container.
Figure 5:
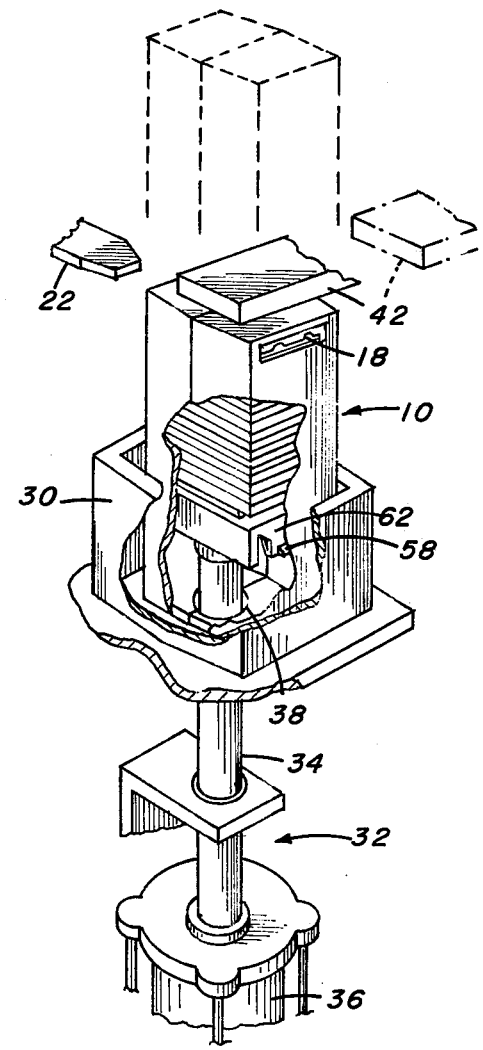
FIG. 5 is a view similar to FIG. 4 with the container inserted into the nest.

Referring to FIGS. 4 and 5, a container 10 is shown with a portion of the analyzer apparatus including both a nest 30 for receiving container 10 and a plunger apparatus 32. The plunger apparatus comprises a rod 34 which extends out of a spring cylinder 36, through a hole 38 in the bottom of nest 30. Resilient means (not shown) in cylinder 36 urge rod 34 upwardly as viewed in FIG. 4 so that, when a container 10 is inserted into nest 30, plunger rod 34 first enters the container through an opening 38 in the rear (or bottom) wall of the container to push against a stack positioning element 40. Further insertion of the container into the nest causes plunger rod 34 to be depressed into cylinder 36 until the container is in its FIG. 5 position, and a clamp 42 is moved over the container to hold it in the nest.

The slide stack rests on a pair of rails 48 and 50 of the stack positioning element. As stack positioning element 40 moves forwardly toward the dispensing station of container 10, a pair of anti-backup member ratchet pawls 56 and 58 engage successive teeth of ratchet teeth sets 52 and 54 respectively to inhibit movement of the slides away from the dispensing station of container 10 should the container be removed from the analyzer nest after some but not all of the slides have been dispensed therefrom. Upon removal of the container, plunger rod 34 is withdrawn from opening 38 so that only the ratchet means keeps the slide stack from falling.

The ratchet pawls are mounted on flexible, resilient arms 60 and 62 which bias the pawls into engagement with teeth 52 and 54 respectively with sufficient force to maintain such engagement when subjected to a reasonable amount of jarring. Additional details of stack positioning element 40 are disclosed in co-assigned U.S. patent application Ser. No. 912,290 entitled ARTICLE DISPENSER APPARATUS, filed concurrently herewith in the names of G. W. Scherer and R. G. Covington.

The invention has been described in detail with particular reference to a preferred embodiment thereof, but it will be understood that variations and modifications can be effected within the spirit and scope of the invention.

What is claimed is:

1. An article container for dispensing reagent articles to apparatus having an extendable plunger and being adapted to use the articles to carry out quantitative chemical analysis of fluid samples; said container comprising:

wall structure forming a chamber having a dispensing station, said chamber being adapted to receive a stack of articles for movement toward, and sequential removal from, said dispensing station for delivery to the apparatus, said wall structure having an opening through which the plunger may extend into said chamber; and a stack positioning element separate from the plunger and captured in said chamber between a received article stack and said opening, said element being engageable and movable by the plunger extending through said opening, toward said dispensing station to urge a received article stack toward said dispensing station, whereby the articles are sequentially indexed into said dispensing station as preceding articles in the stack are removed from said container.

2. The container as set forth in claim 1 further comprising anti-backup means on said stack positioning element cooperable with said wall structure for inhibiting movement of the stack positioning element away from the dispensing station.

3. The container as set forth in claim 2 wherein said anti-backup member includes:

a movable arm attached at one of its ends to the stack positioning element; and a pawl on said arm and spaced from said end for engagement with said wall structure.

4. The container as set forth in claim 3 wherein said wall structure comprises a plurality of ratchet teeth cooperable with the pawl for inhibiting movement of said stack positioning element away from said dispensing station.

5. A container for dispensing reagent articles to apparatus having a plunger and being adapted to use the articles to carry out quantitative chemical analysis of fluid samples, said container comprising:

a plurality of walls forming a chamber for receiving a stack of articles and having an article dispensing station, one of said walls having an opening for receiving the plunger to move the articles toward the dispensing station;

a plurality of ratchet teeth along at least one of the walls; and an element captured in the container between a received stack of articles and the plunger opening, said element including:

(1), pawl means engageable with said ratchet teeth for inhibiting movement of said element away from the dispensing station to prevent movement of the articles away from the dispensing station, and (2) means for urging said pawl means into engagement with said teeth with a predetermined force.

* * * * *